United States Patent
Watanabe (10) Patent No.: US 11,633,574 B2
(45) Date of Patent: *Apr. 25, 2023

(54) GUIDE WIRE

(71) Applicant: TERUMO KABUSHIKI KAISHA, Tokyo (JP)

(72) Inventor: Kohei Watanabe, Fuji (JP)

(73) Assignee: TERUMO KABUSHIKI KAISHA, Tokyo (JP)

(*) Notice: Subject to any disclaimer, the term of this patent is extended or adjusted under 35 U.S.C. 154(b) by 641 days.

This patent is subject to a terminal disclaimer.

(21) Appl. No.: 16/507,276

(22) Filed: Jul. 10, 2019

(65) Prior Publication Data
US 2019/0329006 A1 Oct. 31, 2019

Related U.S. Application Data

(63) Continuation of application No. PCT/JP2018/012134, filed on Mar. 26, 2018.

(30) Foreign Application Priority Data
Mar. 29, 2017 (JP) .............................. JP2017-066368

(51) Int. Cl.
A61M 25/09 (2006.01)
A61B 17/12 (2006.01)

(52) U.S. Cl.
CPC ........ *A61M 25/09* (2013.01); *A61B 17/12109* (2013.01); *A61B 17/12181* (2013.01);
(Continued)

(58) Field of Classification Search
CPC ......... A61M 2025/09066; A61M 2025/09075; A61M 2025/09166; A61M 2025/09175;
(Continued)

(56) References Cited

U.S. PATENT DOCUMENTS 5,120,308 A   6/1992  Hess
5,243,996 A * 9/1993  Hall .................. A61M 25/09
                                              600/585
(Continued)

FOREIGN PATENT DOCUMENTS

CN    102107040 A    6/2011
CN    105517489 A    4/2016
(Continued)

OTHER PUBLICATIONS

Machine translation of JP 2004073252 A (Year: 2022).*
(Continued)

*Primary Examiner* — David J. McCrosky
(74) *Attorney, Agent, or Firm* — Buchanan Ingersoll & Rooney PC (57) ABSTRACT

A guide wire is disclosed, which is capable of reducing an unintended deviation in a guide wire position while preventing an occurrence of discomfort with respect to usability. The guide wire has a flexible core wire, and has a distal core portion, a main body portion, and a rigidity changing portion that gradually decreases in rigidity from the main body portion toward the distal core portion. The rigidity changing portion includes a first tapered portion continuous with a distal end of the main body portion, a second tapered portion continuous with a distal end of the first tapered portion, and a third tapered portion continuous with a proximal end of the distal core portion. A boundary portion between the first tapered portion and the second tapered portion is located in a range of 300 to 400 mm from a foremost distal end of the distal core portion.

20 Claims, 5 Drawing Sheets

(52) U.S. Cl.
CPC .............. *A61M 2025/09066* (2013.01); *A61M 2025/09075* (2013.01); *A61M 2025/09166* (2013.01); *A61M 2025/09175* (2013.01)

(58) Field of Classification Search
CPC .............................. A61M 25/09–0905; A61M 2025/09008–09191
See application file for complete search history.

(56) References Cited

U.S. PATENT DOCUMENTS

| | | | |
|---|---|---|---|
| 5,865,767 A | | 2/1999 | Frechette et al. |
| 6,478,752 B1 * | | 11/2002 | Ishikawa ............... A61M 25/09 600/585 |
| 11,191,924 B2 * | | 12/2021 | Watanabe ......... A61M 25/0133 |
| 2011/0160705 A1 | | 6/2011 | Matsumoto et al. |
| 2016/0206381 A1 | | 7/2016 | Grass et al. |

FOREIGN PATENT DOCUMENTS

| | | | |
|---|---|---|---|
| EP | 1 142 604 A1 | 10/2001 | |
| JP | 2003505116 A | 2/2003 | |
| JP | 2004-073252 A | 3/2004 | |
| JP | 5142229 B2 | 2/2013 | |
| JP | 2013111320 A | 6/2013 | |
| JP | 2016532513 A | 10/2016 | |
| JP | 2016221199 A | 12/2016 | |
| JP | 6159923 B1 | 7/2017 | |
| WO | 00/32265 A1 | 6/2000 | |

OTHER PUBLICATIONS

An English Translation of the International Search Report (Form PCT/ISA/210) and the Written Opinion of the International Searching Authority (Form PCT/ISA/237) dated May 22, 2018, by the Japanese Patent Office in corresponding International Application No. PCT/JP2018/012134. (7 pages).
International Search Report (PCT/ISA/210) and translation and Written Opinion (PCT/ISA/237) dated May 22, 2018, by the Japanese Patent Office as the International Searching Authority for International Application No. PCT/JP2018/012134.
The extended European Search Report dated Dec. 16, 2020, by the European Patent Office in corresponding European Patent Application No. 18777177.9-1132. (7 pages).
Office Action (The First Office Action) dated Mar. 3, 2021, by the National Intellectual Property Administration in corresponding Chinese Patent Application No. 201880007789.X and an English Translation of the Office Action. (11 pages).

* cited by examiner

GUIDE WIRE

CROSS-REFERENCES TO RELATED APPLICATIONS

This application is a continuation of International Application No. PCT/JP2018/012134 filed on Mar. 26, 2018, which claims priority to Japanese Application No. 2017-066368 filed on Mar. 29, 2017, the entire content of both of which is incorporated herein by reference.

FIELD OF THE DISCLOSURE

The present disclosure relates to a guide wire.

BACKGROUND DISCUSSION

In the related art, a catheter device is used to perform a treatment or the like in a body lumen. A guide wire having a flexible core wire is used to guide the catheter device to a target site of the body lumen. For example, a transarterial chemoembolization (TACE) is a treatment method in which a catheter is advanced from an artery of the liver further to the vicinity of a tumor, and an anti-cancer agent or an embolic material is injected to selectively necrosis the tumor. In the TACE, a guide wire is used to advance the catheter.

In order to enhance operability when passing a guide wire into a body lumen, a guide wire can be provided with a rigidity changing portion that gradually decreases in rigidity from a proximal side toward a distal side (for example, see U.S. Pat. No. 5,865,767). The rigidity of the rigidity changing portion is changed by gradually decreasing a diameter of a core wire. Note that the "proximal side" means a side located on an opposite side, when a side introduced into the living body is referred to as a "distal side".

A body lumen has an intricately curved or serpentine shape. Therefore, when a guide wire passes through the body lumen, a large bending load acts on the core wire as a distal portion of the guide wire reaches the deep side.

In the related art of the guide wire, the range in which the rigidity changing portion of the core wire is provided is a range of at most 300 mm from a foremost distal end of the core wire. Therefore, in a case of the procedure in which a target site of treatment is present in the deep side of the body lumen (i.e., a relatively large distance), a large bending load acts on the core wire. The restoring force to return to the original straight state acts on the bent core wire. As a result, when a fixed state of the guide wire is loosened, a position of the guide wire is deviated in a direction to get out of the body. Thus, an unintended deviation in guide wire position can easily occur.

In order to reduce the unintended deviation in guide wire position, it is conceivable to widen a range in which the rigidity changing portion is provided in the core wire toward the proximal side. However, merely widening the range of the rigidity changing portion causes a sense of discomfort in usability by an operator.

SUMMARY

A guide wire is disclosed, which is capable of reducing an unintended deviation in a guide wire position while preventing an occurrence of discomfort with respect to usability.

A guide wire according to the present disclosure includes a flexible core wire, in which the core wire has a distal core portion that includes a foremost distal end and is most flexible in an entire length of the core wire, a main body portion that constitutes a portion more proximal than the distal core portion and has a constant diameter along an axial direction, and a rigidity changing portion that constitutes a portion from a distal end of the main body portion to a proximal end of the distal core portion and gradually decreases in rigidity from the main body portion toward the distal core portion. The rigidity changing portion includes at least a first tapered portion that is continuous with the distal end of the main body portion and has a diameter gradually decreasing from the main body portion toward the distal core portion, a second tapered portion that is continuous with a distal end of the first tapered portion and has a diameter gradually decreasing from the first tapered portion toward the distal core portion, and a n-th tapered portion that is continuous with the proximal end of the distal core portion and has a diameter ($d_n$) gradually decreasing from a $(n-1)$th tapered portion being continuous with the proximal side toward the distal core portion (wherein, $n \geq 3$). Further, a boundary portion between the first tapered portion and the second tapered portion is located in a range of 300 mm to 400 mm from the foremost distal end of the distal core portion, and a gradient $((d_{12}-d_{11})/L_1)$ of a change in the diameter ($d_1$) in the first tapered portion is larger than a gradient $((d_{22}-d_{21})/L_2)$ of a change in the diameter ($d_2$) in the second tapered portion.

In accordance with an exemplary embodiment, by a first tapered portion and a second tapered portion in a rigidity changing portion, a range of the rigidity changing portion in a core wire is longer toward a proximal side beyond, for example, 300 mm from the foremost distal end of the core wire. The gradient of a change in a diameter in the first tapered portion is larger than a gradient of a change in a diameter in the second tapered portion. Therefore, in a unit length in an axial direction, the decrease in the rigidity in the first tapered portion is larger than the decrease in the rigidity in the second tapered portion. As a result, the range having a relatively small rigidity expands in the axial direction as much as possible. Therefore, as in TACE, even when a fixing state of the guide wire is loosened in a case of performing a procedure in which the target site of treatment is present in the deep side of the body lumen, an unintended deviation in the guide wire position can be reduced. Furthermore, the axial direction length of the rigidity changing portion becomes longer without structural modification of the distal core portion and the n-th tapered portion continuous with the proximal end of the distal core portion. The distal core portion and the n-th tapered portion constitute the distal part of the core wire, and are sites that greatly affect the flexibility and usability of the guide wire. Therefore, according to the present disclosure, a guide wire is disclosed, which is capable of reducing an unintended deviation in a guide wire position while preventing an occurrence of discomfort with respect to usability.

In accordance with another exemplary embodiment, a guide wire is disclosed comprising: a flexible distal core portion that includes a foremost distal end; a flexible main body portion that constitutes a portion more proximal than the distal core portion and has a constant diameter along an axial direction; and a rigidity changing portion that constitutes a portion from a distal end of the main body portion to a proximal end of the distal core portion and decreases in rigidity from the main body portion toward the distal core portion, the rigidity changing portion comprising at least: a first tapered portion that is continuous with the distal end of the main body portion and has a diameter decreasing from the main body portion toward the distal core portion; a second tapered portion that is continuous with a distal end of the first tapered portion and has a diameter decreasing from the first tapered portion toward the distal core portion; an n-th tapered portion that is continuous with the proximal end of the distal core portion and has a diameter decreasing from an (n−1)th tapered portion being continuous with the proximal side toward the distal core portion; and a gradient of a change in the diameter in the first tapered portion is larger than a gradient of a change in the diameter in the second tapered portion.

In accordance with a further exemplary embodiment, a guide wire configured for a transarterial chemoembolization is disclosed, the guide wire comprising: a flexible core wire, the flexible core wire comprising: a distal core portion that includes a foremost distal end; a main body portion that constitutes a portion more proximal than the distal core portion and has a constant diameter along an axial direction; and a rigidity changing portion that constitutes a portion from a distal end of the main body portion to a proximal end of the distal core portion and decreases in rigidity from the main body portion toward the distal core portion, the rigidity changing portion having an axial length of 360 mm to 430 mm, and wherein the rigidity changing portion comprises at least: a first tapered portion that is continuous with the distal end of the main body portion and has a diameter decreasing from the main body portion toward the distal core portion; a second tapered portion that is continuous with a distal end of the first tapered portion and has a diameter decreasing from the first tapered portion toward the distal core portion; an n-th tapered portion that is continuous with the proximal end of the distal core portion and has a diameter decreasing from an (n−1)th tapered portion being continuous with the proximal side toward the distal core portion; a boundary portion between the first tapered portion and the second tapered portion is located in a range of 300 mm to 400 mm from the foremost distal end of the distal core portion; and each of the first tapered portion, the second tapered portion, and the n-th tapered portion having a tapered angle that is constant along the axial direction.

DETAILED DESCRIPTION

Hereinafter, an embodiment of the present disclosure will be described with reference to the attached drawings. Note that the following description does not limit the technical scope or the meaning of terms described in the claims.

Further, the dimensional ratios in the drawings are exaggerated for the sake of explanation, and may differ from the actual proportions.

Figure 1A:
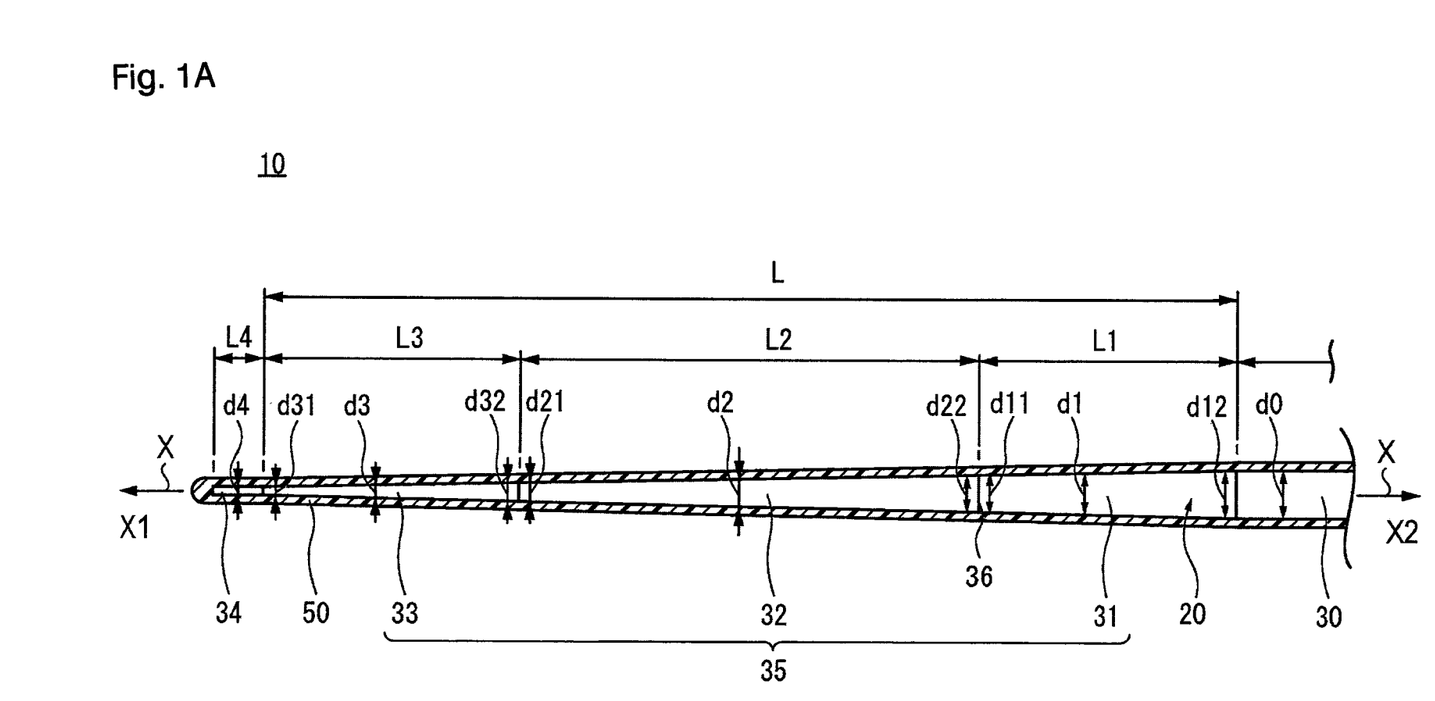
FIG. 1A is an axial direction cross-sectional diagram of a guide wire.
Figure 1B:
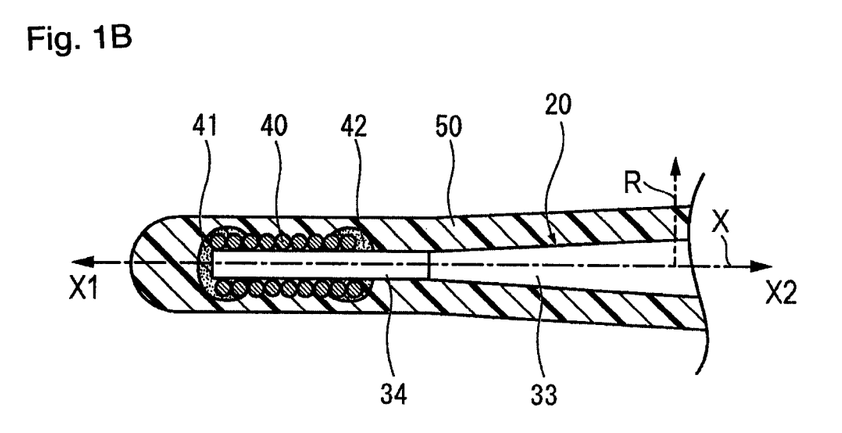
FIG. 1B is an axial direction cross-sectional diagram showing a distal part of the guide wire in an enlarged manner.
Figure 2:
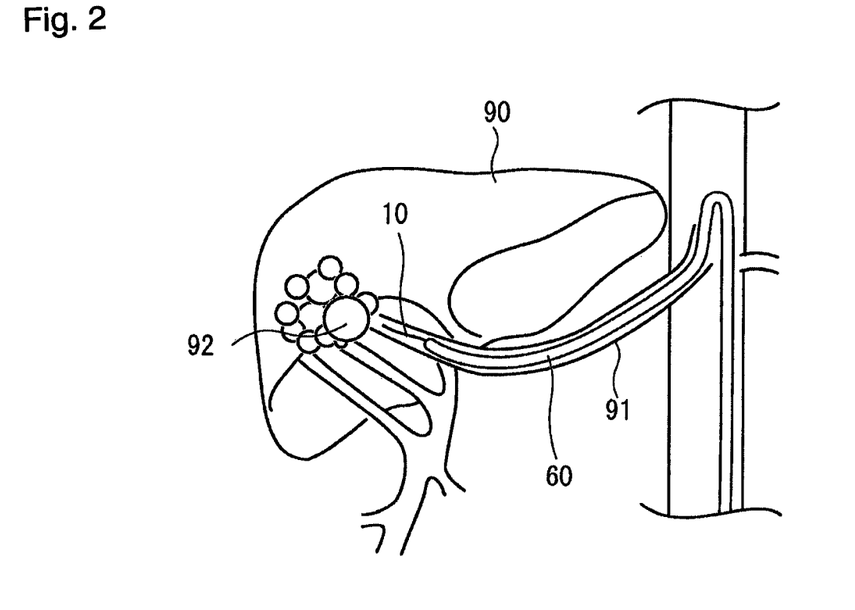
FIG. 2 is a diagram schematically showing an aspect in which a catheter is being advanced along the guide wire in a TACE.

FIG. 1A is an axial direction cross-sectional diagram of a guide wire 10, and FIG. 1B is an axial direction cross-sectional diagram showing a distal part of the guide wire 10 in an enlarged manner. FIG. 2 is a diagram schematically showing an aspect in which a catheter 60 is being advanced along the guide wire 10 in the TACE.

In the description of the present specification, a long-length direction (left and right direction in FIG. 1A) of the core wire 20 of the guide wire 10 is defined as an axial direction, and is indicated by an arrow X in each drawing. A direction orthogonal to the axial direction is defined as a radial direction and is indicated by an arrow R in FIG. 1B. In the guide wire 10, a side to be inserted into a living body (in the blood vessel) is defined as a distal side (distal side, left side in FIG. 1A) and is indicated by an arrow X1 in each drawing, and a side to be operated at the hand located opposite to the distal side is defined as a proximal side (proximal side, right side in FIG. 1A) and is indicated by an arrow X2 in each drawing. In the present specification, a distal portion means a part including a certain range in the axial direction from the distal end (the foremost distal end), and a proximal portion means a part including a certain range in the axial direction from the proximal end (the foremost proximal end).

With regard to a diameter of the core wire 20, as shown, for example, in FIG. 1A, numbers (1, 2, 3) of the suffix "x" represented as a diameter dxy represent a first tapered portion 31, a second tapered portion 32, and a third tapered portion 33, respectively. The numbers (1, 2) of the suffix "y" represent the distal side and the proximal side, respectively. With regard to a flexural load value of the core wire 20, numbers (1, 2, 3) of the suffix "x" represented as a flexural load value fxy represent the first tapered portion 31, the second tapered portion 32, and the third tapered portion 33, respectively. The numbers (1, 2) of the suffix "y" represent the distal side and the proximal side, respectively.

Referring to FIGS. 1A and 1B, the guide wire 10 of the present embodiment has the core wire 20 extending in the axial direction, a marker portion 40 disposed at the distal portion of the core wire 20, and a coating layer 50 coating the core wire 20.

The guide wire 10 is inserted into, for example, a body lumen. In the body lumen, the guide wire 10 is inserted through a lumen (guide wire lumen) of the therapeutic or diagnostic catheter 60. The guide wire 10 is used to guide the catheter 60 to a target site of the body lumen.

For example, as shown in FIG. 2, the transarterial chemoembolization (TACE) is a treatment method in which the catheter 60 is advanced from an artery 91 of the liver 90 further to the vicinity of a tumor 92, and an anti-cancer agent or an embolic material is injected to selectively necrosis the tumor. In the TACE, the guide wire 10 is used to advance the catheter 60.

A body lumen has an intricately curved or serpentine shape. Therefore, when the guide wire 10 passes through the body lumen, a large bending load acts on the core wire 20 as a distal portion of the guide wire 10 reaches the deep side.

Core Wire 20

Figure 3A:
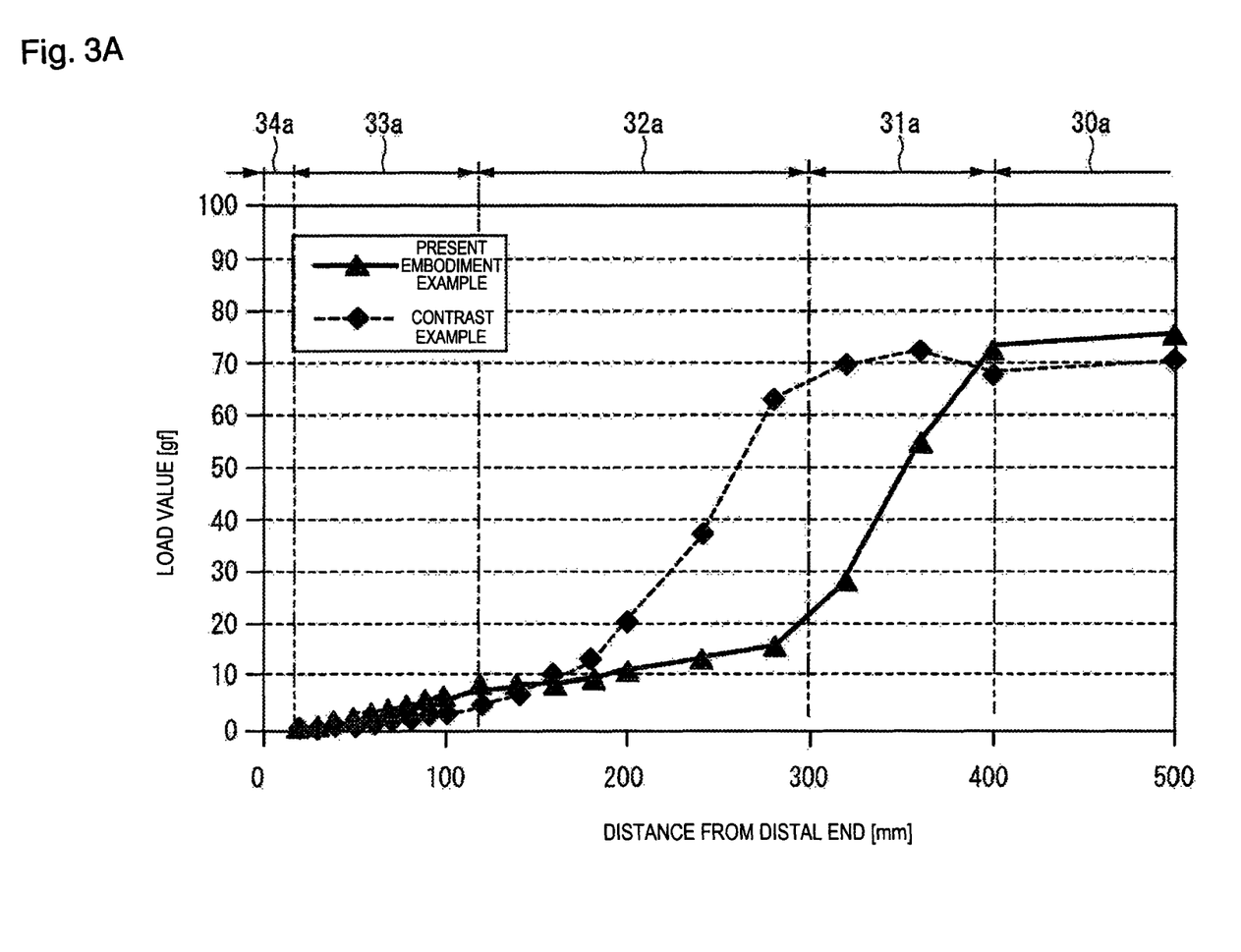
FIG. 3A is a graph showing flexural load values of a core wire of the guide wire along an axial position of the core wire.
Figure 3B:
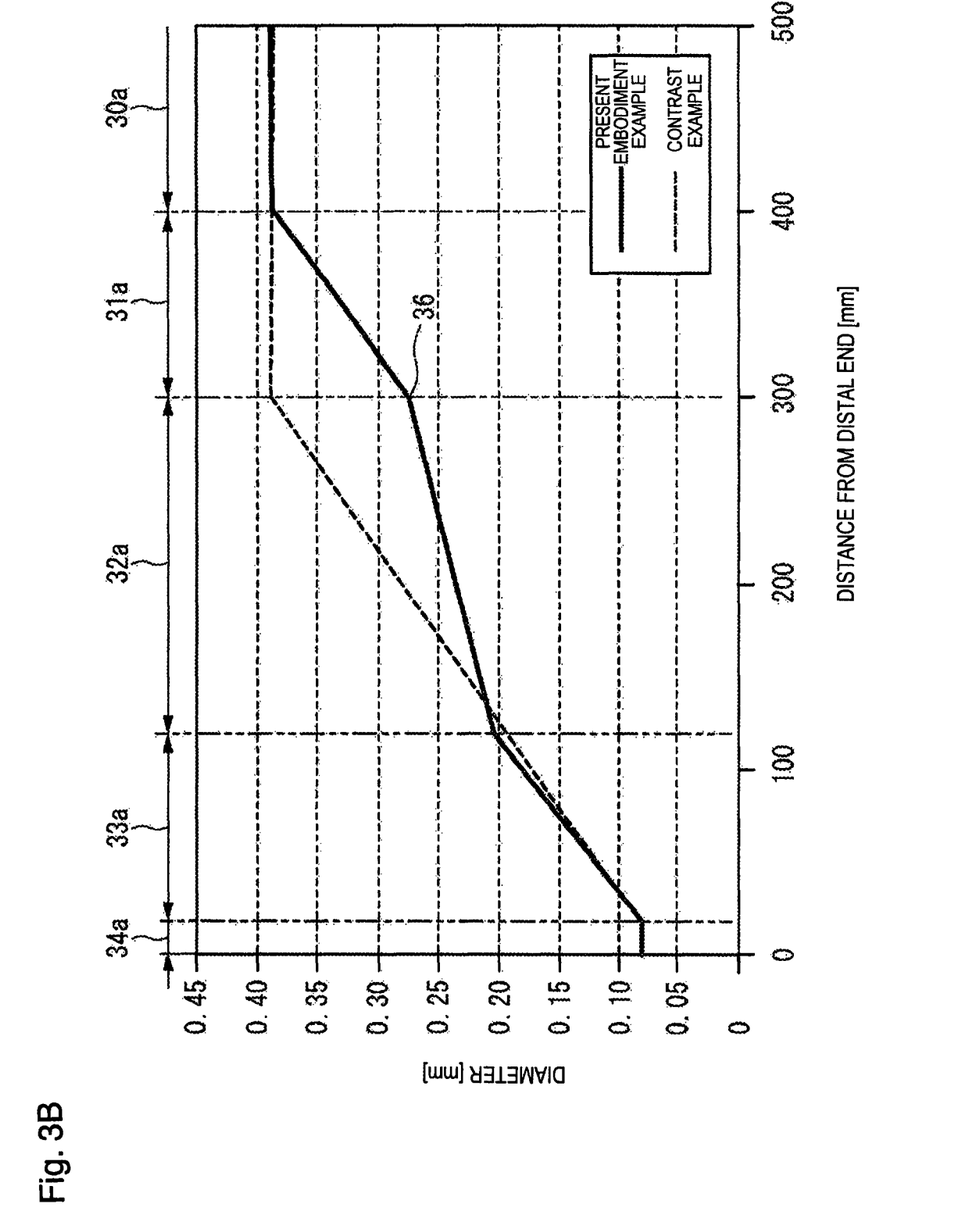
FIG. 3B is a graph showing diameters of the core wire of the guide wire along the axial position of the core wire.

FIG. 3A is a graph showing flexural load values of the core wire 20 of the guide wire 10 along the axial direction position of the core wire 20, and FIG. 3B is a graph showing diameters of the core wire 20 of the guide wire 10 along the axial direction position of the core wire 20.

As shown in FIGS. 1A and 1B, the core wire 20 is flexible, and has the distal core portion 34, the main body portion 30, and the rigidity changing portion 35. In accordance with an exemplary embodiment, including a foremost distal end, the distal core portion 34 is the most flexible site in the entire length of the core wire 20. The main body portion 30 constitutes a portion more proximal than the distal core portion 34 and is a site having a constant diameter d0 along the axial direction. The rigidity changing portion 35 constitutes a portion from the distal end of the main body portion 30 to the proximal end of the distal core portion 34, and is a site that gradually decreases in rigidity from the main body portion 30 toward the distal core portion 34.

In accordance with an exemplary embodiment, the rigidity changing portion 35 includes at least the first tapered portion 31, the second tapered portion 32, . . . , the (n−1)th tapered portion, and the n-th tapered portion 33 (where, n≥3), in order from the proximal side to the distal side. Each of the tapered portions 31, 32, . . . , 33 has a tapered shape that gradually decreases in diameter (inclined to the axial direction). In the illustrated embodiment, the rigidity changing portion 35 includes three tapered portions (n=3). Therefore, the second tapered portion 32 corresponds to the (n−1)th tapered portion. The n-th tapered portion 33 is hereinafter referred to as a "third tapered portion 33".

In FIGS. 3A and 3B, a region of the distal core portion 34 is indicated by a reference numeral 34a, and a region of the main body portion 30 is indicated by a reference numeral 30a. Further, a region of the first tapered portion 31 is indicated by a reference numeral 31a, a region of the second tapered portion 32 is indicated by a reference numeral 32a, and a region of the third tapered portion 33 is indicated by a reference numeral 33a.

In the present embodiment, the core wire 20 is formed of a single material. The diameter of the core wire 20 varies along the axial direction. Thereby, the rigidity of the core wire 20 changes along the axial direction.

The core wire 20 material is not particularly limited, and, for example, a Ni—Ti based alloy, a stainless steel, a super-elastic alloy or the like can be used.

In accordance with an exemplary embodiment, the main body portion 30 has a constant diameter d0 along the axial direction. The distal core portion 34 also has a constant diameter d4 along the axial direction.

In the present specification, "having a constant diameter along the axial direction" does not mean to be limited to a case of physically having the same diameter. In a range in which the rigidity (flexural rigidity or torsional rigidity) of the main body portion 30 or the distal core portion 34 can be made substantially constant, it is sufficient to have a substantially constant outer diameter dimension.

In accordance with an exemplary embodiment, the first tapered portion 31 is continuous with the distal end of the main body portion 30 and has a diameter d1 that gradually decreases from the main body portion 30 toward the distal core portion 34. The second tapered portion 32 is continuous with the distal end of the first tapered portion 31 and has a diameter d2 that gradually decreases from the first tapered portion 31 toward the distal core portion 34. The third tapered portion 33 is continuous with the proximal end of the distal core portion 34, and has a diameter d3 that gradually decreases from the second tapered portion 32 continuous with the proximal side, toward the distal core portion 34.

The boundary portion 36 between the first tapered portion 31 and the second tapered portion 32 is preferably located within, for example, a range of 300 mm to 400 mm from the foremost distal end of the distal core portion 34. Furthermore, it is preferable that the gradient ((d12−d11)/L1) of the change in the diameter d1 in the first tapered portion 31 is larger than the gradient ((d22−d21)/L2) of the change in the diameter d2 in the second tapered portion 32. As shown in FIG. 3B, in the present embodiment, the boundary portion 36 is set, for example, at a position of 300 mm from the foremost distal end of the distal core portion 34.

In FIGS. 3A and 3B, the flexural load values and the diameters in the core wire of the contrast example are indicated by broken lines. In the contrast example, the length of the rigidity changing portion is, for example, 280 mm, and the start point of the proximal side of the rigidity changing portion is, for example, 300 mm from the foremost distal end.

As shown in FIG. 3B, in the contrast example, a range of the rigidity changing portion in the core wire is, for example, up to 300 mm from the foremost distal end of the core wire. On the other hand, in the present embodiment, by the first tapered portion 31 and the second tapered portion 32 in the rigidity changing portion 35, the range of the rigidity changing portion 35 in the core wire 20 is longer toward the proximal side, for example, beyond 300 mm from the foremost distal end of the core wire 20.

The gradient ((d12−d11)/L1) of the change in the diameter d1 in the first tapered portion 31 is larger than the gradient ((d22−d21)/L2) of the change in the diameter d2 in the second tapered portion 32. From this, as shown in FIG. 3A, in a unit length in the axial direction, the decrease in the rigidity in the first tapered portion 31 is larger than the decrease in the rigidity in the second tapered portion 32. As a result, the range having a relatively small rigidity expands in the axial direction as much as possible.

Furthermore, the axial direction length of the rigidity changing portion 35 becomes longer without structural modification (change in diameter, material, or the like) of the distal core portion 34 and the third tapered portion 33 continuous with the proximal end of the distal core portion 34. The distal core portion 34 and the third tapered portion 33 constitute the distal part of the core wire 20, and are sites that greatly affect the flexibility and usability of the guide wire 10. Therefore, even if the axial direction length of the rigidity changing portion 35 is changed, an occurrence of discomfort in usability by the operator is relatively small.

As shown in FIG. 3B, the gradient Δ3 (=(d32−d31)/L3) of the change in the diameter d3 in the third tapered portion 33 of the present embodiment is substantially the same as the gradient of the change in the diameter in the rigidity changing portion in the contrast example. In other words, the gradient Δn (=(dn2−dn1)/Ln) of the change in the diameter do in the n-th tapered portion is substantially the same with respect to the gradient Δ0 (=(d0−d4)/(300−axial direction length of the distal core portion)) of the change in the diameter determined by the distal end diameter d0 of the main body portion and the proximal end diameter d4 of the distal core portion when the range of the rigidity changing portion is, for example, up to 300 mm from the foremost distal end of the distal core portion. The axial direction length of the distal core portion 34 is, for example, 20 mm, and the length of the rigidity changing portion of the contrast example is, for example, 280 mm as described above.

As shown in FIG. 3A, the third tapered portion 33 continuous with the proximal side of the distal core portion 34 has substantially the same change in the flexural load values along the axial direction as the core wire in which the range of rigidity changing portion is, for example, up to 300 mm from the foremost distal end of the distal core portion (core wire of the contrast example). As the change in the flexural load values along the axial direction greatly affects the flexibility and usability of the guide wire 10, as described above, even if the axial direction length of the rigidity changing portion 35 is changed, an occurrence of discomfort in usability by the operator is relatively small.

The ratio of the gradients (Δn/Δ0) is not limited to approximately one, and can be freely set within a range that does not cause a sense of discomfort in the usability by the operator. From this point of view, it is preferable, for example, that the ratio of gradients (Δn/Δ0) be 0.27≤Δn/Δ0≤1.80. If the ratio of the gradients (Δn/Δ0) is less than 0.27, the change in the rigidity of the core wire 20 is relatively poor, so that an unintended deviation in the guide wire 10 position is likely to occur. If the ratio of the gradients (Δn/Δ0) exceeds 1.80, the change in rigidity of the core wire 20 is relatively too large, and the operability of the guide wire 10 can be reduced. Therefore, the above range is preferable.

In accordance with an exemplary embodiment, the diameter d12 of the proximal side of the first tapered portion 31 is substantially the same as the diameter d0 of the main body portion 30 so that the boundary between the main body portion 30 and the first tapered portion 31 is a continuous surface. Similarly, the diameter d22 of the proximal side of the second tapered portion 32 is substantially the same as the diameter d11 of the distal side of the first tapered portion 31. The diameter d32 of the proximal side of the third tapered portion 33 is substantially the same as the diameter d21 of the distal side of the second tapered portion 32. The diameter d4 of the distal core portion 34 is substantially the same as the diameter d31 of the distal side of the third tapered portion 33.

In the present specification, "continuous surface" means that an outer surface of the core wire 20 is smooth to the extent that the guide wire 10 does not get caught on an inner wall of the body lumen or the catheter 60. For example, when the diameter d12 of the proximal side of the first tapered portion 31 and the diameter d0 of the main body portion 30 are not formed substantially the same, a slight level difference is generated at the boundary between the first tapered portion 31 and the main body portion 30. However, by a coating layer 50, the outer surface of the guide wire 10 may be a substantially smooth surface, and the guide wire 10 may not be caught by the inner wall of the body lumen or the like. In such a case, even if the core wire 20 has a slight level difference, the outer surface of the core wire 20 can be regarded as a "continuous surface".

In accordance with an exemplary embodiment, a tapered angle (inclination angle to the axial direction of a tapered shape) of the first tapered portion 31 is constant along the axial direction. The tapered angle of the second tapered portion 32 is constant along the axial direction. The tapered angle of the third tapered portion 33 is constant along the axial direction.

Note that the tapered angle of each tapered portion 31, 32, and 33 can be changed along the axial direction. For example, when viewed in a cross section along the axial direction, the tapered angle can be changed so that a central part, for example, of the tapered portion 31, 32, and 33, bulges outward in a convex shape rather than a linear shape when the tapered angle is constant.

Any combination may be made, for example, in such a manner that the tapered angles of the first tapered portion 31 and the third tapered portion 33 are constant along the axial direction and the tapered angle of the second tapered portion 32 is changed along the axial direction.

In accordance with an exemplary embodiment, the core wire 20 is formed by performing a cutting process or a polishing process for a forming material. The respective regions of the main body portion 30, the first tapered portion 31, the second tapered portion 32, the third tapered portion 33, and the distal core portion 34 can be simultaneously formed. In accordance with an exemplary embodiment, respective regions may be formed separately and sequentially. The manufacture of the core wire 20 is not limited to the cutting process or the polishing process, and can be, for example, formed by an etching or a laser process.

When the tapered angle is made constant along the axial direction, each tapered portion 31, 32, and 33 can be formed relatively more easily as compared with a case where the tapered angle is changed along the axial direction.

One example of dimensional specifications of the main body portion 30, the first tapered portion 31, the second tapered portion 32, the third tapered portion 33, and the distal core portion 34 is as shown in Table 1 below.

TABLE 1

| Region | Diameter [mm] | Axial Length [mm] | Gradient of Change in Diameter (Diameter Variation/Length) |
|---|---|---|---|
| Distal core portion 34 | Diameter d4: 0.080 | L4 = 20 | — |
| Third tapered portion 33 | Distal side diameter d31 (=d4) Proximal side diameter d32: 0.210 | L3 = 100 | 0.0013 |
| Second tapered portion 32 | Distal side diameter d21 (=d32) Proximal side diameter d22: 0.275 | L2 = 180 | 0.000361 |
| First tapered portion 31 | Distal side diameter d11 (=d22) Proximal side diameter d12 (=d0) | L1 = 100 | 0.00125 |
| Main body portion 30 | Diameter d0: 0.400 | (Depending on product length) | — |

Referring to FIG. 3B and Table 1, the gradient ((d12−d11)/L1) of the change in the diameter d1 in the first tapered portion 31 is larger than the gradient ((d22−d21)/L2) of the change in the diameter d2 in the second tapered portion 32.

Regarding the diameters d1, d2, and d3 of the respective tapered portions 31, 32 and 33, any of the following (1) to (3) can be said.

(1) It is preferable that the diameter d11 of the distal side in the first tapered portion 31 is, for example, 45% to 75% of the diameter d0 of the main body portion 30. In the example of Table 1, 0.275/0.40≈0 0.688. If the diameter d11 is, for example, less than 45% of the diameter d0, the core wire 20 becomes relatively too soft, and the operability of the guide wire 10 can be reduced. If the diameter d11 exceeds, for example, 75% of the diameter d0, the rigidity of the core wire 20 is relatively too high, so that an unintended deviation in the guide wire 10 position is likely to occur when the fixed state of the guide wire 10 is loosened. Therefore, the above range can be preferable.

(2) It is preferable that the gradient ((d12−d11)/L1) of the change in the diameter d1 in the first tapered portion 31 is, for example, 3.4 to 21.7 times the gradient ((d22−d21)/L2)

of the change in the diameter d2 in the second tapered portion 32. In the example of Table 1, 0.00125/0.000361≈3.46. If the gradient of the change in the diameter d1 is, for example, less than 3.4 times the gradient of the change in the diameter d2, the change in the rigidity of the core wire 20 is relatively poor, so that an unintended deviation in the guide wire 10 position is likely to occur. If the gradient of the change in the diameter d1, for example, exceeds 21.7 times the gradient of the change in the diameter d2, the change in rigidity of the core wire 20 is relatively too large, and the operability of the guide wire 10 can be reduced. Therefore, the above range is preferable.

(3) It is preferable that the change (d12−d21) in diameter in the first tapered portion 31 and the second tapered portion 32 is, for example, 1.4 times to 7.1 times the change (d32−d31) in the diameter in the third tapered portion 33. In the example of Table 1, (0.400−0.210)/(0.210−0.080)≈1.46. If the change in diameter in the first tapered portion 31 and the second tapered portion 32 is, for example, less than 1.4 times the change in diameter in the third tapered portion 33, the change in the rigidity of the core wire 20 is relatively poor, so an unintended deviation in the guide wire 10 position is likely to occur. If the change in diameter in the first tapered portion 31 and the second tapered portion 32, for example, exceeds 7.1 times the change in diameter in the third tapered portion 33, the rigidity change of the core wire 20 is relatively too large, and the operability of the guide wire 10 can be reduced. Therefore, the above range can be preferable.

The relationships of the above (1) to (3) based on the dimensional specifications of the respective regions are equivalent to the relationships based on the flexural load values. The flexural load value is obtained by a flexural load value measurement.

Figure 4:
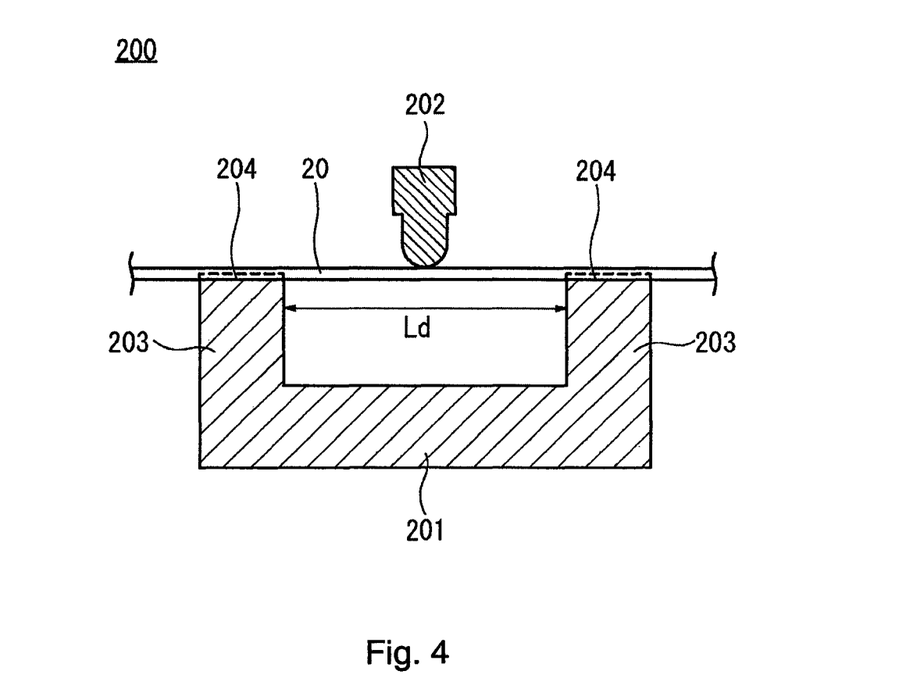
FIG. 4 is a cross-sectional diagram showing a schematic configuration of a measurement test device for measuring a flexural load value of the core wire of the guide wire.

FIG. 4 is a cross-sectional diagram showing a schematic configuration of a measurement test device 200 for measuring a flexural load value of the core wire 20 of the guide wire 10.

Referring to FIG. 4, the measurement test device 200 has a fixing jig 201 for supporting the core wire 20 and a pushing-down jig 202 disposed above the fixing jig 201. The fixing jig 201 has a pair of supporting legs 203 for supporting the core wire 20 at two points. The interval Ld between the supporting legs 203 is, for example, 25.4 mm. An upper surface of the supporting legs 203 is formed with a groove portion 204 into which the core wire 20 is fit. The pushing-down jig 202 is configured to be freely movable in an up-and-down manner with respect to the fixing jig 201. The pushing-down jig 202 is configured to freely adjust the speed at which the core wire 20 is pushed down and the dimension at which the core wire 20 is pushed down.

In the present embodiment, using the measurement test device 200, a flexural load value measurement is performed under the following conditions to obtain a flexural load value. That is, the core wire 20 is supported at two points, for example, with a 25.4 mm gap. The pushing-down jig 202 moves at a speed, for example, of 5 mm/min. The supported central part of the core wire 20 is vertically pushed down by the pushing-down jig 202. The flexural load value is obtained by measuring the load when the core wire 20 is pushed down by 2 mm, for example. Since it is necessary to support the core wire 20 at two points, the measurement of the flexural load value is started from a position, for example, 20 mm from the foremost distal end of the core wire 20. The measurement start position is a position of the distal end of the third tapered portion 33. In FIG. 3A, measurement values from a position 20 mm from the foremost distal end of the core wire 20 are plotted.

One example of flexural load values of the main body portion 30, the first tapered portion 31, the second tapered portion 32, and the third tapered portion 33 is as shown in Table 2 below.

TABLE 2

| Region | Flexural Load Value [gf] | Position from Distal End [mm] | Gradient of Change in Rigidity (Flexural Load Value Variation/Length) |
|---|---|---|---|
| Third tapered portion 33 | Flexural load value near distal end f31: 0.4 | 20 (Note 1) | 0.065 (Note 2) |
| | Flexural load value of proximal side f32: 6.9 | 120 | |
| Second tapered portion 32 | Flexural load value of distal side f21 (=f32) | 120 | 0.10 |
| | Flexural load value of proximal side f22: 25.2 | 300 | |
| First tapered portion 31 | Flexural load value of distal side f11 (=f22) | 300 | 0.55 |
| | Flexural load value of proximal side f12 (=f0) | 400 | |
| Main body portion 30 | Flexural load value f0: 79.8 | 400 | — |

(Note 1)
It is a position of a distal end of a third tapered portion 33. A load value at this position is referred to as "flexural load value near distal end f31".
(Note 2)
A length, for example, is 100 mm which is a measureable range.

Regarding the flexural load values f1, f2, and f3 of the respective tapered portions 31, 32 and 33, any of the following (4) to (6) can be said.

(4) Regarding the flexural load value obtained by the flexural load value measurement, it is preferable that a flexural load value f11 of the distal side in the first tapered portion 31 is, for example, 13% to 36% of a flexural load value f0 of the main body portion 30. In the example of Table 2, 25.2/79.8≈0.316. If the flexural load value f11 is, for example, less than 13% of the flexural load value f0, the core wire 20 becomes relatively too soft, and the operability of the guide wire 10 can be reduced. If the flexural load value f11 exceeds, for example, 36% of the flexural load value f0, the rigidity of the core wire 20 is relatively too high, so that an unintended deviation in the guide wire 10 position is likely to occur. Therefore, the above range is preferable.

(5) Regarding the flexural load value obtained by the flexural load value measurement, it is preferable that a gradient ((f12−f11)/L1) of the change in the flexural load value f1 in the first tapered portion 31 is, for example, 5.3 times to 17.8 times the gradient ((f22−f21)/L2) of the change in the flexural load value f2 in the second tapered portion 32. In the example of Table 2, 0.55/0.10≈5.5. If the gradient of the change in the flexural load value f1 is, for example, less than 5.3 times the gradient of the change in the flexural load value f2, the change in the rigidity of the core wire 20 is relatively poor, so that an unintended deviation in the guide wire 10 position is likely to occur. If the gradient of the change in the flexural load value f1 exceeds, for example, 17.8 times the gradient of the change in the flexural load value f2, the change in rigidity of the core wire 20 is relatively too large, and the operability of the guide wire 10 can be reduced. Therefore, the above range is preferable.

(6) Regarding the flexural load value obtained by the flexural load value measurement, it is preferable that the flexural load value f21 of the distal side in the second tapered portion 32 is, for example, 2.0 times to 22.3 times the flexural load value f31 near the distal end in the third tapered portion 33, and the flexural load value f12 of the proximal side in the first tapered portion 31 is, for example, 187 times to 239 times the flexural load value f31 near the distal end of the third tapered portion 33. In the example of Table 2, the former f21/f31 is 6.9/0.4=17.3 and the latter f12/f31 is 79.8/0.4≈199.5. If f21/f31 is, for example, less than 2.0 times, the change in the rigidity of the core wire 20 is relatively poor, so that an unintended deviation in the guide wire 10 position is likely to occur. If f21/f31 exceeds, for example, 22.3 times, the change in rigidity of the core wire 20 is relatively too large, and the operability of the guide wire 10 can be reduced. Further, if f12/f31 is, for example, less than 187 times, the rigidity of the distal core portion 34 is relatively high, and the risk of vascular damage increases. If f12/f31 exceeds, for example, 239 times, the change in rigidity of the core wire 20 is relatively too large, and the operability of the guide wire 10 can be reduced. Therefore, the above range is preferable.

In the present embodiment, the axial direction length of the core wire 20 has a length suitable for use in the TACE. In this case, the axial direction length L (L1+L2+L3) of the rigidity changing portion 35 (the first tapered portion 31, the second tapered portion 32, and the third tapered portion 33) is preferably, for example, 360 mm to 430 mm or 360 mm to 400 mm. By using the rigidity changing portion 35 of the length L, the region of the core wire 20 reaching the site from the aorta to the common hepatic artery (300 mm to 400 mm from the distal end) becomes relatively flexible, thereby the TACE can be suitably performed.

The boundary portion 36 between the first tapered portion 31 and the second tapered portion 32 is, for example, in a range of 200 mm to 400 mm from the distal end of the distal core portion 34, more preferably, for example, in a range of 250 mm to 350 mm from the distal end of the distal core portion 34, and still more preferably, the boundary portion 36 between the first tapered portion 31 and the second tapered portion 32, for example, is located in a range of 280 mm to 320 mm from the distal end of the distal core portion 34.

The axial direction length L1 of the first tapered portion 31, for example, is 80 mm to 230 mm, more preferably 80 mm to 170 mm, still more preferably 80 mm to 120 mm, and 100 mm is particularly preferable. By using the first tapered portion 31 of the axial direction length L1, the region of the core wire 20 reaching the site from the aorta to the common hepatic artery (for example, 300 mm to 400 mm from the distal end) becomes relatively flexible, thereby the TACE can be suitably performed.

Further, in accordance with an exemplary embodiment, the axial direction length L2 of the second tapered portion 32, for example, is 160 mm to 280 mm, more preferably 160 to 220 mm, still more preferably 160 mm to 200 mm, and 180 mm is particularly preferable. By using the second tapered portion 32 of the axial direction length L2, the region of the core wire 20 reaching the site from the common hepatic artery to the proper hepatic artery and further to the left and right hepatic artery (for example, 100 mm to 300 mm from the distal end) becomes relatively flexible, thereby the TACE can be suitably performed.

The position of the boundary portion 36 between the first tapered portion 31 and the second tapered portion 32 described above, the length of the first tapered portion 31, and the length of the second tapered portion 32 are based on sensory test results when the TACE is performed using a model that simulates the liver 90.

Marker Portion 40

Referring to FIG. 1B, a marker portion 40 is disposed to cover the distal core portion 34 in a certain range extending in the axial direction. The marker portion 40 is configured with a wire wound in a spiral shape around the distal core portion 34. The distal portion of the marker portion 40 is fixed near the distal portion of the distal core portion 34 through the fixing material 41. The proximal portion of the marker portion 40 is fixed near the proximal portion of the distal core portion 34 through the fixing material 42. The fixing materials 41 and 42 can be made of, for example, various adhesives, solder, or the like.

The marker portion 40 is made of a material having radiopacity (radiopaque property). Examples of a material having the radiopacity include metal materials such as noble metals such as gold, platinum, tungsten or alloys containing noble metals (for example, platinum-iridium alloy). By providing the marker portion 40 in the distal core portion 34, the guide wire 10 can be inserted into a living body while confirming the position of the distal portion of the guide wire 10 under radioscopy.

Coating Layer 50

The coating layer 50 is made of a resin material and formed so as to cover the entire core wire 20 including the marker portion 40. The distal portion of the coating layer 50 is preferably a rounded shape so as not to damage the inner wall of the body lumen.

In accordance with an exemplary embodiment, the coating layer 50 is preferably made of a material that can reduce friction. Thereby, the frictional resistance (sliding resistance) with the catheter 60 through which the guide wire 10 is inserted or the body lumen is reduced and the sliding performance can be improved, and the operability of the guide wire 10 can be improved. Further, since the sliding resistance of the guide wire 10 is reduced, it is possible to more reliably prevent kinks (bend) or twists of the guide wire 10.

The resin material constituting the coating layer 50 is preferably a material having relatively high flexibility, for example, polyolefin such as polyethylene and polypropylene, polyvinyl chloride, polyester (PET, PBT, or the like), polyamide, polyimide, polyurethane, polystyrene, polycarbonate, silicone resins, fluorine-based resins (PTFE, ETFE, PFA, or the like), composite materials thereof, various rubber materials such as latex rubber and silicone rubber, or composite materials obtained by combining two or more in these which is mentioned above. Among the above materials, it is more preferable to use a urethane resin from the viewpoint of further improving the flexibility. As a result, the distal portion of the guide wire 10 can be made flexible, so that it is possible to prevent the inner wall of the body lumen from being damaged when inserting the guide wire 10 into the body lumen.

The thickness of the coating layer 50 is not particularly limited, and is preferably, for example, 5 μm to 500 μm. Note that the coating layer 50 is not limited to a single layer structure, and may be configured by laminating a plurality of layers.

Hydrophilic Coating Layer

The coating layer 50 is preferably covered with a hydrophilic coating layer not shown. Since the sliding performance is improved by being covered by the hydrophilic coating layer, the guide wire 10 can be further prevented from being caught on the inner wall of the body lumen or the catheter 60.

The hydrophilic coating layer material is not particularly limited, and for example, well-known hydrophilic substances may be mentioned, such as a cellulose-based polymer substance, polyethylene oxide polymer substance, maleic anhydride-based polymer substance (for example, maleic anhydride copolymer such as methyl vinyl ether-maleic anhydride copolymer), acrylamide-based polymer substance (for example, block copolymers of polyacrylamide, polyglycidyl methacrylate-dimethyl acrylamide (PGMA-DMAA)), water soluble nylon, polyvinyl alcohol, and polyvinyl pyrrolidone.

The thickness of the hydrophilic coating layer is not particularly limited, and is preferably, for example, 0.1 µm to 100 µm.

Action and Effect

The guide wire 10 of the present embodiment has the following actions and effects.

The core wire 20 in the guide wire 10 arranges the boundary portion 36 between the first tapered portion 31 and the second tapered portion 32 in a range of 300 mm to 400 mm from the foremost distal end of the distal core portion 34, and sets a gradient d1 (($d_{12}-d_{11}$)/L1) of the change in the diameter d1 in the first tapered portion 31 larger than a gradient (($d_{22}-d_{21}$)/L2) of the change in the diameter d2 in the second tapered portion 32.

In this way, by the first tapered portion 31 and the second tapered portion 32 in the rigidity changing portion 35, the range of the rigidity changing portion 35 in the core wire 20 is longer toward the proximal side beyond, for example, 300 mm from the foremost distal end of the core wire 20. The gradient (($d_{12}-d_{11}$)/L1) of the change in the diameter d1 in the first tapered portion 31 is larger than the gradient (($d_{22}-d_{21}$)/L2) of the change in the diameter d2 in the second tapered portion 32. Therefore, in a unit length in the axial direction, the decrease in the rigidity in the first tapered portion 31 is larger than the decrease in the rigidity in the second tapered portion 32. As a result, the range having a relatively small rigidity expands in the axial direction as much as possible. Therefore, as in TACE, even when the fixing state of the guide wire 10 is loosened in a case of performing a procedure in which the target site of treatment is present in the deep side of the body lumen, an unintended deviation in the guide wire 10 position can be reduced. Furthermore, the axial direction length of the rigidity changing portion 35 becomes longer without structural modification of the distal core portion 34 and the third tapered portion 33 continuous with the proximal end of the distal core portion 34. The distal core portion 34 and the third tapered portion 33 constitute the distal part of the core wire 20, and are sites that greatly affect the flexibility and usability of the guide wire 10. Therefore, according to the present embodiment, it is possible to provide a guide wire 10 capable of reducing an unintended deviation in a guide wire 10 position while preventing an occurrence of discomfort with respect to usability.

The gradient $\Delta 3$ (=($d_{32}-d_{31}$)/L3) of the change in the diameter d3 in the third tapered portion 33 is $0.35 \leq \Delta n / \Delta 0 \leq 2.11$ with respect to the gradient $\Delta 0$ (=($d_0-d_4$)/(300−axial direction length of the distal core portion)) of the change in the diameter determined by the distal end diameter d0 of the main body portion and the proximal end diameter d4 of the distal core portion when the range of the rigidity changing portion is up to 300 mm from the foremost distal end of the distal core portion.

The change in the flexural load value along the axial direction greatly affects the flexibility and usability of the guide wire 10. With such a configuration, even when the length of the rigidity changing portion 35 is set to a length exceeding, for example, 300 mm, the change in the flexural load value along the axial direction in the vicinity of the distal end (distal core portion 34 and third tapered portion 33) is substantially the same as when the length of the rigidity changing portion is, for example, 300 mm. For this reason, compared with the time of using the guide wire whose length of the rigidity changing portion is, for example, 300 mm, discomfort does not occur in usability. Therefore, it is possible to provide a guide wire 10 capable of reducing an unintended deviation in a guide wire 10 position while preventing an occurrence of discomfort with respect to usability.

Regarding the diameter of each tapered portion, by satisfying any of the following conditions (1) to (3), it is possible to reduce an unintended deviation in the guide wire 10 position while preventing an occurrence of discomfort in usability.

(1) The diameter d11 of the distal side in the first tapered portion 31 is, for example, 45% to 75% of the diameter d0 of the main body portion 30.

(2) The gradient d1 (($d_{12}-d_{11}$)/L1) of the change in diameter d1 in the first tapered portion 31 is, for example, 3.4 times to 21.7 times the gradient (($d_{22}-d_{21}$)/L2) of the change in the diameter d2 in the second tapered portion 32.

(3) The change ($d_{12}-d_{21}$) in diameter in the first tapered portion 31 and the second tapered portion 32 is, for example, 1.4 times to 7.1 times the change ($d_{32}-d_{31}$) in the diameter in the third tapered portion 33.

The relationships among the above (1) to (3) are equivalent to the relationships based on the flexural load values. Therefore, regarding the flexural load values, by satisfying any of the following conditions (4) to (6), it is possible to reduce an unintended deviation in the guide wire 10 position while preventing an occurrence of discomfort in usability.

(4) Regarding the flexural load value obtained by the flexural load value measurement, the flexural load value f11 of the distal side in the first tapered portion 31 is, for example, 13% to 36% of the flexural load value f0 of the main body portion 30.

(5) Regarding the flexural load value obtained by the flexural load value measurement, the gradient (($f_{12}-f_{11}$)/L1) of the change in the flexural load value f1 in the first tapered portion 31 is, for example, 5.3 times to 17.8 times the gradient (($f_{22}-f_{21}$)/L2) of the change in the flexural load value f2 in the second tapered portion 32.

(6) Regarding the flexural load value obtained by the flexural load value measurement, the flexural load value f21 of the distal side in the second tapered portion 32 is, for example, 2.0 times to 22.3 times the flexural load value f31 near the distal end in the third tapered portion 33, and the flexural load value f12 of the proximal side in the first tapered portion 31 is, for example, 187 times to 239 times the flexural load value f31 near the distal end of the third tapered portion 33.

The core wire 20 is formed of a single material.

With this configuration, the core wire 20 can be rather easily manufactured as compared with a case where the distal core portion 34, the rigidity changing portion 35, and the main body portion 30 are formed of different materials and joined.

The tapered angle of the first tapered portion 31 is constant along the axial direction.

With this configuration, the first tapered portion 31 can be easily formed as compared with a case where the tapered angle is changed along the axial direction.

The tapered angle of the second tapered portion 32 is constant along the axial direction.

With this configuration, the second tapered portion 32 can be easily formed as compared with a case where the tapered angle is changed along the axial direction.

The tapered angle of the third tapered portion 33 is constant along the axial direction.

With this configuration, the third tapered portion 33 can be rather easily formed as compared with a case where the tapered angle is changed along the axial direction.

In accordance with an exemplary embodiment, the core wire 20 has a length suitable for use in the TACE. The axial direction length L of the rigidity changing portion 35 can be, for example, 360 mm to 430 mm.

With this configuration, when performing the TACE, the region of the core wire 20 reaching the site (for example, 300 to 400 mm from the distal end) from the aorta to the proper hepatic artery becomes flexible, thereby it is possible to reduce an unintended deviation in the guide wire 10 position while preventing an occurrence of discomfort in usability.

When the axial direction length L of the rigidity changing portion 35 is, for example, set to 360 mm to 430 mm, the axial direction length L1 of the first tapered portion 31 is, for example, 80 mm to 230 mm.

By using the first tapered portion 31 with the axial direction length L1, the TACE can be more suitably performed.

When the axial direction length L of the rigidity changing portion 35 is, for example, set to 360 mm to 430 mm, the axial direction length L2 of the second tapered portion 32 is, for example, 160 mm to 280 mm.

By using the second tapered portion 32 with the axial direction length L2, the TACE can be more suitably performed.

Although the guide wire 10 according to the present disclosure has been described through the embodiment, the present disclosure is not limited only to each configuration demonstrated in this specification, and it is possible to change suitably based on the statement of claims.

For example, although the guide wire 10 used for the TACE has been mentioned as an example, the guide wire 10 of the present disclosure can be used in other procedures.

Although the embodiment in which the rigidity changing portion 35 is configured with three tapered portions has been described (for example, n=3), the rigidity changing portion 35 may be configured, for example, with four or more tapered portions.

Although the embodiment has been described in which the rigidity is changed along the axial direction by forming the core wire 20 from a single material and changing the diameter along the axial direction (that is, making the guide wire with a tapered shape), the present disclosure is not limited to the case. By using different materials for each constituent material of the main body portion 30, a plurality of rigidity changing portions 35, and the distal core portion 34, the rigidity can be changed along the axial direction. The main body portion 30, the plurality of rigidity changing portions 35, and the distal core portion 34 which are using different constituent materials can be joined by an appropriate known method such as welding, deposition, or adhesion. Each portion of the core wire 20 may be formed by combining the use of different constituent materials and the forming in a tapered shape.

The detailed description above describes embodiments of a guide wire. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A guide wire comprising:
    a flexible core wire, the flexible core wire comprising:
        a distal core portion that includes a foremost distal end of the flexible core wire, the distal core portion having a constant diameter along an axial direction, the distal core portion being most flexible in an entire length of the core wire;
        a main body portion that constitutes a portion more proximal than the distal core portion and has a constant diameter along the axial direction; and
        a rigidity changing portion having a continuous taper that constitutes a portion from a distal end of the main body portion to a proximal end of the distal core portion and decreases in rigidity from the main body portion toward the distal core portion, the rigidity changing portion comprising at least:
            a first tapered portion that is continuous with the distal end of the main body portion and has a diameter decreasing from the main body portion toward the distal core portion;
            a second tapered portion that is continuous with a distal end of the first tapered portion and has a diameter decreasing from the first tapered portion toward the distal core portion; and
            one or more third tapered portions, the one or more third tapered portions being continuous with a distal end of the second tapered portion on a proximal end of the one or more third tapered portions and continuous with the proximal end of the distal core portion on a distal end of the one or ore third tapered portions, and the one or more third tapered portions having a diameter decreasing from the second tapered portion toward the distal core portion;
        a boundary between the first tapered portion and the second tapered portion being located 300 mm to 400 mm from the foremost distal end of the distal core portion; and
        a gradient of a change in the diameter in the first tapered portion is larger than a gradient of a change in the diameter in the second tapered portion.

2. The guide wire according to claim 1, wherein a relationship of a gradient of a change in a diameter in the one or more third tapered portions with respect to a gradient of a change in a diameter, determined by a distal end diameter of the main body portion and a proximal end diameter of the distal core portion when a range of the rigidity changing portion is up to 300 mm from the foremost distal end of the distal core portion, satisfies $0.27 \leq \Delta n/\Delta 0 \leq 1.80$, wherein the $\Delta n$ is the gradient of the change in the diameter in the one or more third tapered portions and the $\Delta 0$ is the gradient of the change in the diameter, determined by the distal end diameter of the main body portion and the proximal end diameter of the distal core portion.

3. The guide wire according to claim 1, wherein a diameter of a distal side in the first tapered portion is 45% to 75% of the diameter of the main body portion.

4. The guide wire according to claim 1, wherein the gradient of the change in the diameter in the first tapered portion is 3.4 times to 21.7 times the gradient of the change in the diameter in the second tapered portion.

5. The guide wire according to claim 1, wherein a change in a diameter from a proximal end of the first tapered portion to a distal end of the second tapered portion is 1.4 times to 7.1 times a change in a diameter of the one or more third tapered portions.

6. The guide wire according to claim 1, wherein a flexural load value obtained by a flexural load value measurement in which the core wire is supported at two points with 25.4 mm gap and a load is measured when a supported central part is vertically pushed down by 2 mm by a pushing-down jig moving at a speed of 5 mm/min, a flexural load value of the distal side in the first tapered portion is 13% to 36% of a flexural load value of the main body portion.

7. The guide wire according to claim 1, wherein a flexural load value obtained by a flexural load value measurement in which the core wire is supported at two points with 25.4 mm gap and a load is measured when a supported central part is vertically pushed down by 2 mm by a pushing-down jig moving at a speed of 5 mm/min, a gradient of a change in a flexural load value in the first tapered portion is 5.3 times to 17.8 times a gradient of a change in a flexural load value in the second tapered portion.

8. The guide wire according to claim 1, wherein a flexural load value obtained by a flexural load value measurement in which the core wire is supported at two points with 25.4 mm gap and a load is measured when a supported central part is vertically pushed down by 2 mm by a pushing-down jig moving at a speed of 5 mm/min, a flexural load value of a distal side in the second tapered portion is 2.0 to 22.3 times a flexural load value at a position of 20 mm from a distal end in the one or more third tapered portions, and a flexural load value of a proximal side in the first tapered portion is 187 times to 239 times the flexural load value at the position of 20 mm from the distal end in the one or more third tapered portions.

9. The guide wire according to claim 1, wherein the core wire is formed of a single material.

10. The guide wire according to claim 1, wherein a tapered angle of the first tapered portion is constant along the axial direction.

11. The guide wire according to claim 1, wherein a tapered angle of the second tapered portion is constant along the axial direction.

12. The guide wire according to claim 1, wherein a tapered angle of the one or more third tapered portions is constant along the axial direction.

13. The guide wire according to claim 1, wherein the core wire has a length suitable for use in a transarterial chemo-embolization.

14. The guide wire according to claim 1, wherein an axial direction length of the rigidity changing portion is 360 mm to 430 mm.

15. The guide wire according to claim 14, wherein an axial direction length of the first tapered portion is 80 to 230 mm.

16. The guide wire according to claim 14, wherein an axial direction length of the second tapered portion is 160 mm to 280 mm.

17. The guide wire according to claim 1, wherein the one or more third tapered portions comprises one tapered portion.

18. The guide wire according to claim 1, wherein the one or more third tapered portions comprises two or more tapered portions.

19. A guide wire comprising:
a flexible distal core portion that includes a foremost distal end, the distal core portion having a constant diameter along an axial direction;
a flexible main body portion that constitutes a portion more proximal than the distal core portion and has a constant diameter along the axial direction; and
a rigidity changing portion having a continuous taper that constitutes a portion from a distal end of the main body portion to a proximal end of the distal core portion and decreases in rigidity from the main body portion toward the distal core portion, the rigidity changing portion comprising at least:
a first tapered portion that is continuous with the distal end of the main body portion and has a diameter decreasing from the main body portion toward the distal core portion;
a second tapered portion that is continuous with a distal end of the first tapered portion and has a diameter decreasing from the first tapered portion toward the distal core portion; and
one or more third tapered portions, the one or more third tapered portions being continuous with a distal end of the second tapered portion on a proximal end of the one or more third tapered portions and continuous with the proximal end of the distal core portion on a distal end of the one or more third tapered portions, and the one or more third tapered portions having a diameter decreasing from the second tapered portion toward the distal core portion; and
a gradient of a change in the diameter in the first tapered portion is larger than a gradient of a change in the diameter in the second tapered portion.

20. A guide wire comprising:
a flexible core wire, the flexible core wire comprising:
a distal core portion that includes a foremost distal end of the flexible core wire, the distal core portion having a constant diameter along an axial direction;
a main body portion that constitutes a portion more proximal than the distal core portion and has a constant diameter along the axial direction; and
a rigidity changing portion having a continuous taper that constitutes a portion from a distal end of the main body portion to a proximal end of the distal core portion and decreases in rigidity from the main body portion toward the distal core portion, the rigidity changing portion having an axial length of 360 mm to 430 mm, and wherein the rigidity changing portion comprises at least:
a first tapered portion that is continuous with the distal end of the main body portion and has a diameter decreasing from the main body portion toward the distal core portion;
a second tapered portion that is continuous with a distal end of the first tapered portion and has a diameter decreasing from the first tapered portion toward the distal core portion;
one or more third tapered portions, the one or more third tapered portions being continuous with a distal end of the second tapered portion on a proximal end of the one or more third tapered portions and continuous with the proximal end of the distal core portion on a distal end of the one or more third tapered portions, and the one or more third tapered portions having a diameter decreasing from the second tapered portion toward the distal core portion;

a boundary between the first tapered portion and the second tapered portion being located 300 mm to 400 mm from the foremost distal end of the distal core portion, and wherein a gradient of a change in a flexural load value in the first tapered portion is 5.3 times to 17.8 times a gradient of a change in a flexural load value in the second tapered portion; and the first tapered portion, the second tapered portion, and the one or more third tapered portions having a tapered angle that is constant along the axial direction.

* * * * *